United States Patent [19]  [11] 4,001,940
Cusato  [45] Jan. 11, 1977

[54] ELASTIC POSITIONER APPARATUS FOR ORTHODONTISTS

[75] Inventor: Anthony J. Cusato, Closter, N.J.

[73] Assignee: Henry Mann, Inc., Huntingdon Valley, Pa.

[22] Filed: Feb. 19, 1975

[21] Appl. No.: 550,983

[52] U.S. Cl. .............................. 32/40 R; 32/14 R; 29/229; 81/5.1 R
[51] Int. Cl.² .......................................... A61C 3/00
[58] Field of Search ............... 32/14 R, 14 A, 40 R, 32/66, 63, 64; 81/3 R, 3 E, 5.1 R, 9.3, 418, 427; 128/303 A, 321, 326, 327, 354; 29/235, 229

[56] References Cited

UNITED STATES PATENTS

| 955,955 | 4/1910 | Engelsman | 81/43 |
| 1,974,106 | 9/1934 | Gardella | 128/354 |

FOREIGN PATENTS OR APPLICATIONS

| 523,365 | 10/1953 | Belgium | 29/229 |
| 921,015 | 3/1963 | United Kingdom | 29/235 |
| 764,150 | 12/1956 | United Kingdom | 29/229 |

Primary Examiner—Louis G. Mancene
Assistant Examiner—Jack Q. Lever
Attorney, Agent, or Firm—Ralph R. Roberts

[57] ABSTRACT

This invention pertains to an elastic positioner apparatus on which is mounted, stretched and maintained, in an expanded open position, elastic bands as used in orthodontics. In particular, this apparatus is an elastic positioner which is easily manipulated and on which the expanded elastic bands may be manipulated to maintain arch wires in position on retaining clips mounted on teeth. In another application of use the apparatus may be used to mount elastic bands mounted on teeth so as to expand tooth spacing.

2 Claims, 28 Drawing Figures

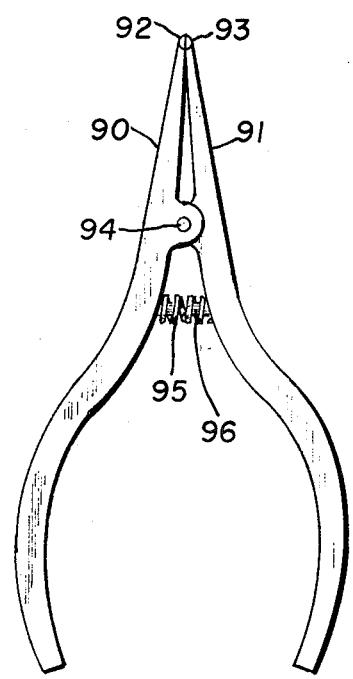
FIG. 14
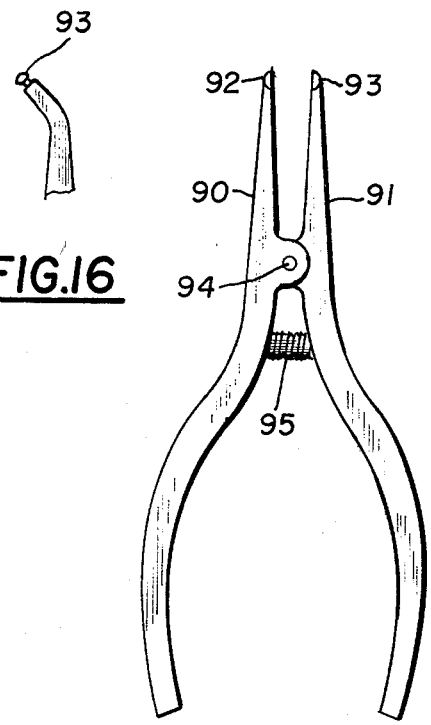
FIG. 16
FIG. 15
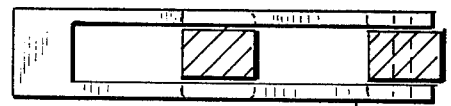
FIG. 19
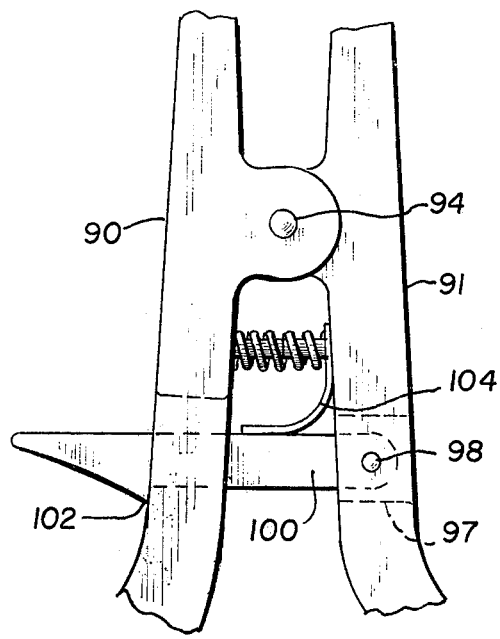
FIG. 17
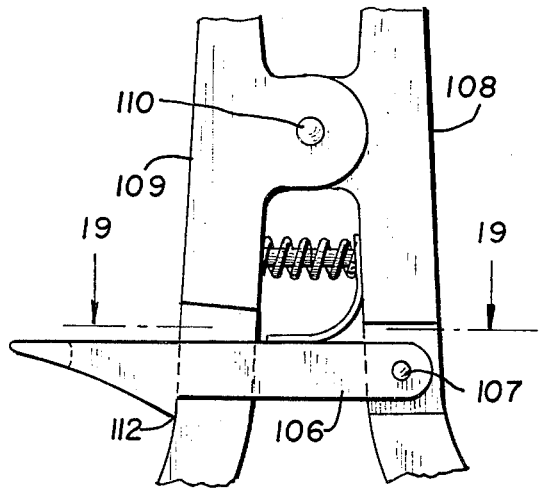
FIG. 18

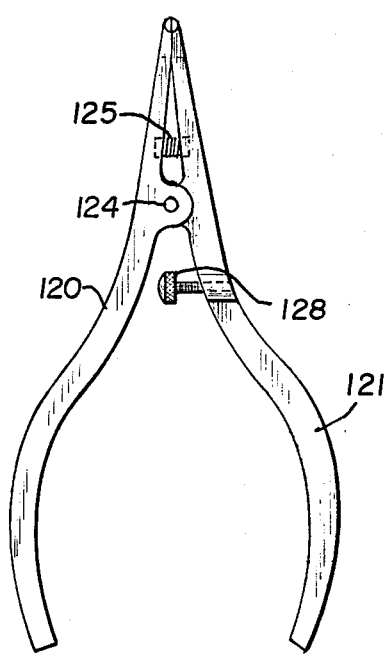
FIG. 20
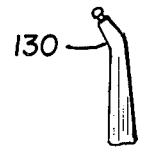
FIG. 22
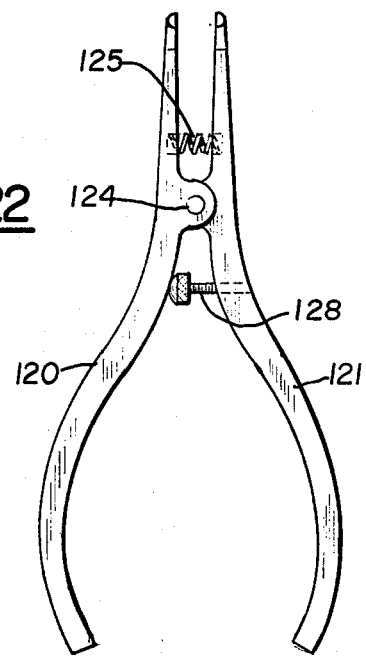
FIG. 21
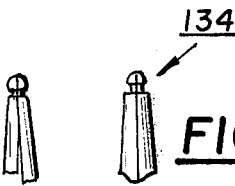
FIG. 23  FIG. 24
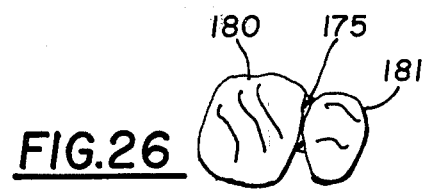
FIG. 25
FIG. 26
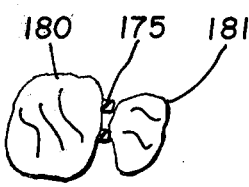
FIG. 27

ELASTIC POSITIONER APPARATUS FOR ORTHODONTISTS

BACKGROUND OF THE INVENTION

1. Field of the Invention

With reference to the classification of art as established in the United States Patent Office the present invention is found in the general Class identified as "Dentistry" (Class 32) and more particularly in the subclass identified as "orthodontic devices" (subclass 14R) and the subclass "corrective accessories" (subclass 14E).

2. Description of the Prior Art

In the field of orthodontics there is widespread use of very small elastic bands to hold arch wires in place on brackets fastened to children's teeth. Elastic bands are also used for separating teeth prior to band placement or impression. Prior to this invention these elastic bands have been stretched manually and by small nose pliers and hemostats. The stretching of these small bands by tools not particularly suited to stretch and hold them is both difficult to achieve and also to maintain during the time of insertion. Often times the band mounting is initially started by hand manipulation and then is completed by a single ended instrument. This method is not only time consuming but also, to a certain extent, frustrating to the orthodontist as he tries to install an arch wire or to install the small rings in the manner of a sep-a-ring (trademark T.P. Laboratories). Nicking of rings often occurs causing the ring to weaken or break. In the present invention a tweezer-type apparatus and a plier-type apparatus are provided in which the jaw end pair portions are formed into small ovoid contours and adjacent thereto a retaining groove which permits easy insertion into the formed band before stretching to an open position. The adjacent grooves formed in the tips retain the elastic band in the desired close proximity to the end of the jaws while said jaws are moved to a determined open position as established either by a stop or by a locking latch.

SUMMARY OF THE INVENTION

This invention may be summarized at least in part with reference to its objects.

It is an object of this invention to provide, and it does provide, a mechanical manipulating device in which a pair of jaws have their ends contoured and sized for the easy insertion into a small elastic band used in orthodontics. The ovoid end portions of the jaws of this positioner apparatus, when in the closed position, are easily slid into the interior of the band and into a groove recess in which the band is retained in close proximity to the ends of the jaws. The jaws are then manipulated to an open condition where a stop or a locking means is provided to hold these bands in an expanded condition for the easy insertion on to clamps to retain arch wires or as a means of applying sep-a-rings for positioning and separating teeth being treated by an orthodontist.

It is a further object of this invention to provide, and it does provide, a plier-type device in which the jaws are contoured to receive and sized for mounting thereon and retaining the small elastic rings prior to these rings being stretched. The manipulation of the jaws to a determined stop establishes the maximum stretch to the bands. In one embodiment there is provided a latching means for holding the jaws in an open condition and in another arrangement an adjustable stop is provided to establish the maximum opening of the jaw.

In a preferred embodiment a tweezer-type device has the movable jaw ends contoured to provide an ovoid shape and receive the elastic band. By means of a latch the jaws are swung to an open and retained position whereby the elastic band is at its selected maximum open condition ready for mounting. At the time of mounting, the latch is manipulated to allow the elastic to return to its gripping condition when mounted on the wire retaining bracket clip or between teeth to actually cause the teeth to separate.

The orthodontic instrument of this invention provides a pair of jaws arranged either as a tweezer or as a plier-type instrument in which the jaw ends are made very narrow and thin. The tip ends of these jaws are ovoid in configuration and are sized to permit easy insertion into an unstretched small elastic band which after passing the ovoid ends move into adjacent grooves. A shoulder at this groove provides a stop means for retaining of the band as it is stretched to a condition where it may be easily applied to an arch wire retainer or clip or as a separating band for urging teeth apart. The jaws may be portions of a tweezer-like instrument or may be the front jaw portions of a plier-like instrument with or without a latching means to retain the jaws in a determined open position. In one embodiment of the plier-like instrument an adjustable stop is provided to limit the outward movement of the jaws.

In addition to the above summary the following disclosure is detailed to insure adequacy and aid in understanding of the invention. This disclosure, however, is not intended to prejudice each new inventive concept therein no matter how it may later be disguised by variations in form or additions of further improvements. For this reason there has been chosen a specific embodiment of a tweezer-type apparatus and an alternate plier-type apparatus and instrument as adopted for use in mounting elastic bands. These embodiments have been chosen for the purpose of illustration and description as shown in the accompanying drawings wherein:

BRIEF DESCRIPTION OF THE DRAWINGS

FIG. 14 represents a side view of an alternate elastic postioner in which instead of a tweezer-type construction, above described, incorporates a plier-type device and like the tweezer-type apparatus the jaw ends of this plier-type apparatus are ovoid shaped and grooved to receive the rubber bands in the manner of the tweezer apparatus of FIGS. 1 and 2;

FIG. 15 shows the plier-type device of FIG. 14 and with the plier in its maximum open condition as provided by stops secured by the handle portions of the pliers;

FIG. 16 represents a side view of the ends of the plier-type device of FIGS. 14 and 15 and showing an approximately thirty degree diagonal displacement of the axis of the jaws from the normal plane of the handles of the pliers;

FIG. 17 represents in an enlarged view a latching device which may be used with a plier-type device such as seen in FIG. 14, this view showing only a fragmentary portion of the jaws and handles in order to show the latching mechanism employed;

FIG. 18 represents a side view of the latching apparatus similar to that of FIG. 17 but instead of an internal latching arrangement there is provided an external latch mounted on the handle portions;

FIG. 19 represents a sectional view taken on the line 19-19 of FIG. 18 and looking in the direction of the arrows;

FIG. 20 represents a side view of an alternate plier-type device in which an adjustable stop is carried by the handle portions and a spring opening means is provided in the jaw portions;

FIG. 21 represents a side view of the plier-type device of FIG. 20 with the jaws moved to their open condition by means of the spring-opening means and as limited by an adjustable stop means;

FIG. 22 represents a fragmentary side view of the contoured jaw ends of the apparatus of FIGS. 20 and 21 and showing the jaws on a bend slightly from the normal plane of the handles;

FIG. 23 represents a fragmentary side view of a pair of contoured jaw ends of thin construction and tapered down to the receiving groove for the elastic rings;

FIG. 24 represents a fragmentary side view of the jaw ends having heavier construction adapted for rubber rings of greater tensile strength, these heavier jaws adapted to easily accommodate the forces necessary to stretch these small O-type elastic rings;

FIG. 25 represents a typical full-size view of elastic bands prior to stretching;

FIG. 26 represents a typical use of a rubber band as stretched and placed between adjacent teeth to cause separation, and FIG. 27 represents a diagrammatic view of the teeth of FIG. 26 after the rubber band has caused the desired separation of the teeth to be accomplished.

In the following description and in the claims various details will be identified by specific names for convenience. The names, however, are intended to be generic in their application. Corresponding reference characters refer to like members throughout the several figures of the drawings.

The drawings accompanying this specification disclose certain details of construction for the purpose of explanation but it should be understood that structural details may be modified in various respects without departure from the concept and that the invention may be incorporated in other structural forms than shown.

Figure 1:
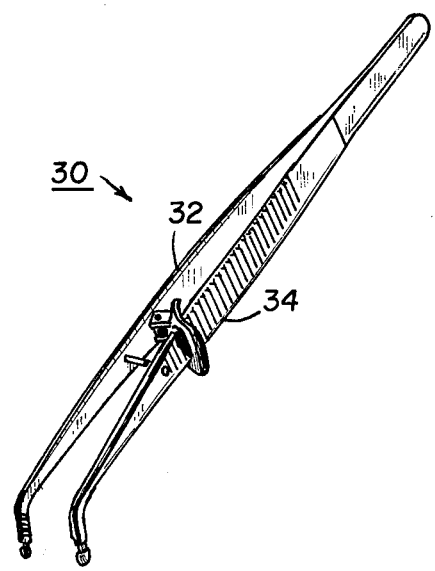
FIG. 1 represents an isometric view of a tweezer-type elastic positioner in which the jaw or leg members are shown in an opened position.
Figure 2:
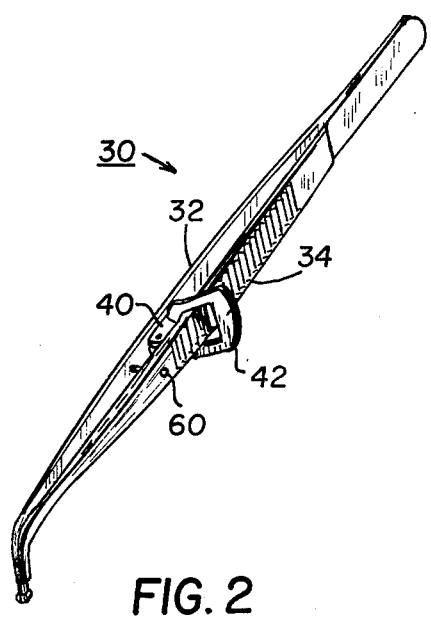
FIG. 2 represents an isometric view of the tweezer-type elastic positioner of FIG. 1 with the jaws in the closed position.
Figure 3:
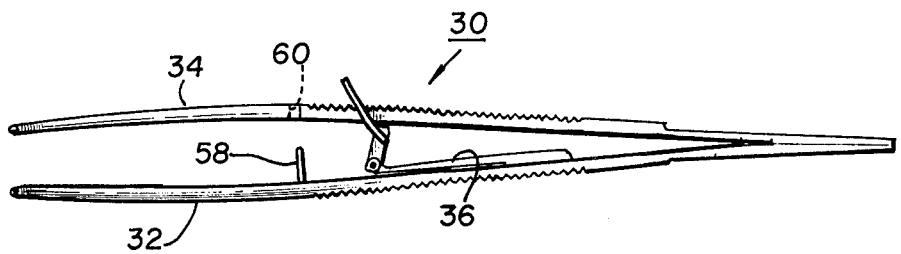
FIG. 3 represents the side view of the tweezer-type positioning apparatus of FIG. 1 in which the hinged end of the latch block is mounted on a spring member secured at its other end to a leg of the tweezer.

DESCRIPTION OF THE PREFERRED EMBODIMENT of FIGS. 1 through 3

Referring now to FIGS. 1 through 3, there is shown a tweezer-type elastic postioner 30 in which a tweezer is shown as normally constructed and with jaw members 32 and 34 in a normally closed condition. The distal or free end of these jaws of this tweezer are preferably bent at about thirty-degrees to forty-five degrees from the plane of the axis of the handle so as to facilitate visual manipulation of the tweezer into the mouth of the patient. In the embodiments shown in FIGS. 1, 2 and 3 one jaw or leg 32 of the tweezer carries a spring-leaf member 36 attached to the inner surface. The free end of this spring member 36 is formed with a hinged leaf 38 on which is pivotally mounted a cam support block 40. This support block 40 is more clearly seen in an enlarged view shown in FIG. 6, to be hereinafter more fully described. To the upper end of this support block is secured a manipulating U-shaped bar which is slidable over and along the upper leg 34 of the tweezer.

Figure 5:
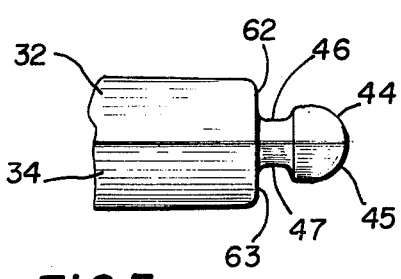
FIG. 5 represents a side view in an enlarged scale and showing the ovoid configured end of the tweezer and with the jaws in a closed condition.
Figure 5A:
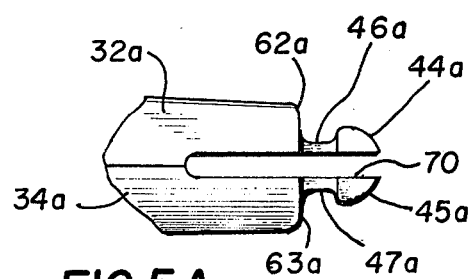
FIG. 5A represents an alternate construction of the jaw ends of FIG. 5 in which the ovoid ends are provided with a small slot into which the end of a wire may enter, this wire providing means upon which the rubber bands are or may be stored.

As seen in FIG. 5A the jaw ends 44 and 45 of the tweezer of FIG. 1 and 3 are reduced in size and are made with substantially ovoid configuration. Inwardly of the rounded ends and adjacent thereto is an undercut 46 and 47 whose inner surface provides a shoulder stop to limit the inward movement of the elastic bands mounted thereon. As seen in FIG. 2, the tweezer 30 is in a closed condition with the U-shape 42 moved to a rear condition so that the tweezer-jaws are in an open condition. When this U-shaped bar 42 is moved forward the jaw ends are brought together as in FIG. 5. The tweezer of FIGS. 1, 2 and 3 is normally closed. By manipulation of and the rotation of the cam support block 40 to a forward condition the tweezer ends are caused to be opened.

Figure 6:
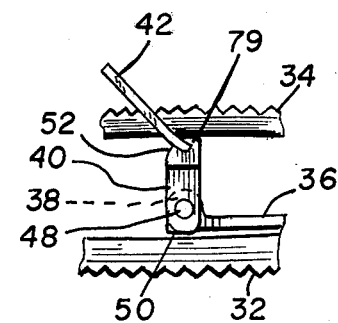
FIG. 6 represents an enlarged side view of the latch block of the tweezer-type apparatus of FIGS. 1 and 2.

As seen particularly in FIG. 6, in an enlarged scale, the camming and latch apparatus includes a leaf spring member 36 whose one end, as seen in FIG. 3, is secured to the tweezer jaw. The free end of the left end of this spring member 36 is formed with a hinge pivot retaining end 30 through which a hinge pin 48 passes and is fixed. The cam block 40 has its slower end bifurcated and pierced to provide a hinge leaf portion when pin 48 has been passed therethrough. The bottom end of block 40 has a flat support surface 50 so that when the block 40 is brought to a substantially vertical condition, as seen in FIG. 6, the cam block 40 tends to stay in this seated condition. The upper end of cam block 40 is rounded at 52 to provide a camming and lifting action as the block 40 is swung in a counterclockwise direction around pin 48. The manipulating bar 42 has its upper cross portion above the leg 34 and its lower two ends are secured to the block member 40 in a fixed manner. The opening 53, as seen in FIG. 2, is formed in member 42 so that it is slidable over and along the upper leg 34 of the tweezer as this cam block is manipulated into open and closed condition.

ALTERNATE CONSTRUCTION OF THE TWEEZER-TYPE ELASTIC POSITIONER AS SEEN IN FIG. 4

Figure 4:
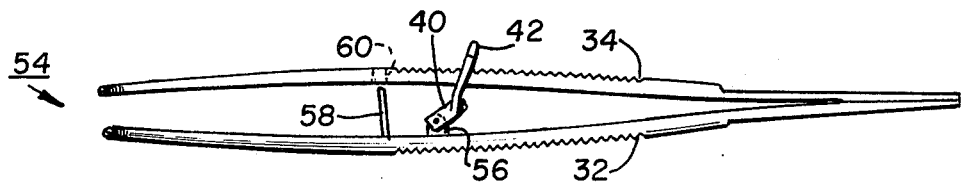
FIG. 4 represents a side view of a tweezer-type positioner similar to that of FIG. 3 but with the latch block hingedly secured directly to a leg of the tweezer.

As seen in FIG. 4, a tweezer-type elastic positioner similar to that shown in the embodiment of FIGS. 1, 2 and 3 is provided. In this particular embodiment, instead of the cam support block 40 carried by a spring member 36 the hinge support for this member is fixedly fixed to the lower leg 32. This fixed hinge portion is identified as 56. In this particular embodiment with the fixed hinge portion supporting the cam block 40 the cam action provided by the manipulation of the U-bar 42 results in a slightly less smooth but easily manipulated operation. Otherwise, the tweezer of FIG. 4 operates in the manner of FIG. 1. It is to be noted that in both the embodiments of FIGS. 1 and 4 there is provided and depicted a guide pin 58 which passes through an aperture 60 formed in the opposite leg member. This guide pin assures and maintains an alignment of the ends of the two leg members 32 and 34 as they are brought into a closed condition so that the small elastic band may be positioned thereon.

ELASTIC BAND ENGAGING AND RETAINING ENDS AS SEEN IN FIGS. 5 AND 5A

Depicted in FIGS. 5 and 5A are the ends of the tweezers of FIGS. 1 and 4. These ends are shown in the closed condition with each end shaped as one-half of a small substantially ovoid or spherical configuration. At the distal end and immediately adjacent the ovoid shape is a reduced diameter groove portion which terminates at a shoulder 62. As seen in FIG. 5, the spherical end portions 44 and 45 are formed of a sufficiently small size to easily enter into and pass through the inside diameter of a small elastic band. The band is slightly expanded as the spherical, ovoid end of the jaws are passed through with the curved end portions providing the cam means to slightly expand the band and as this elastic band is brought to the undercut groove portions 46 and 47 the band returns to its normally formed condition. This residual bias of the band causes it to seat in the undercut groove portions 45 and 47, as seen in FIG. 5. The shoulders 62 and 63 formed on the ends of the tweezer legs 32 and 34 limit and inhibit the inward movement of the small elastic band as it is mounted on the end of the tweezer.

As seen in FIG. 5A, in the formed ends of the legs 32 and 34 of the tweezer of FIGS. 1 and 4 there is formed a slot 70 which preferably is substantially centrally positioned as to the axis of the legs 32 and 34. This slot 70 is of a determined selected width and extends a short distance into the end portions 32a and 34a of the tweezer ends with this slot extending a short distance passed the shoulders 62a and 63a. These spherical or ovoid end portions 44a and 45a are similar to the portions shown in FIG. 5 and include the undercut portions 62a and 63a which are also substantially identical with the undercut 46 and 47 shown in FIG. 5. The use of the slot 70 is described in conjunction with the embodiments of FIGS. 7, 8, 9 and 10.

ELASTIC BAND STORAGE DEVICE OF FIG. 7

Figure 7:
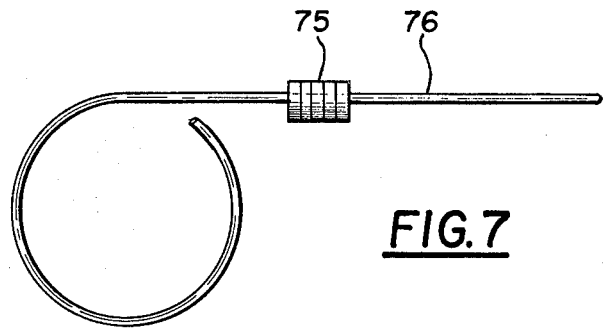
FIG. 7 depicts a wire and a grouping of rubber bands which are slidably mounted upon this wire, this wire configuration providing one means of storage of the bands, the wire end inteval into the slot formed in the jaw ends of FIG. 5B; this wire having wire storage means having a manipulating loop for grasping and guiding of the wire.

In FIG. 7 there is shown a conventional storage device for a group of elastic bands identified as 75. A wire 76 has a straight portion and for the purpose of grasping hand manipulation has a curled portion which may or may not contain a substantial grouping of the elastic bands 75. The diameter of the wire 76 is slightly less than that other groove width 70 shown in the tweezer end of FIG. 5A.

Figure 8:
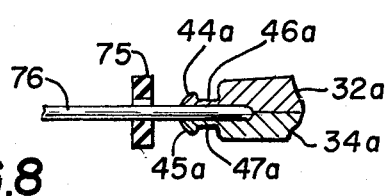
FIG. 8 represents a sectional view of the jaw ends similar to that shown in FIG. 5A in which the wire receiving slot between the jaw ends receives the wire of the storage device of FIG. 7 with a rubber band ready for mounting onto the jaw ends.
Figure 9:
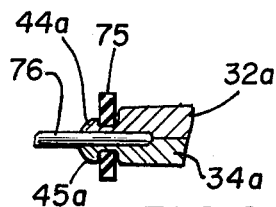
FIG. 9 represents the sectional view of the jaw ends and rubber band mounted on the wire of FIG. 8 and showing the rubber band moved forward on the wire and over the configured jaw end engaging portion.
Figure 10:
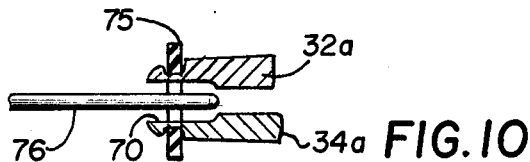
FIG. 10 represents the sectional view of the jaw ends of FIG. 8 and FIG. 9 with the jaw ends beginning to be opened to stretch the seated rubber band and with the end of the wire storage device ready for removal from between the jaws.

MOUNTING OF THE ELASTIC BAND ON THE TWEEZER JAW AS SEEN IN FIGS. 8, 9 and 10

As seen in FIGS. 8, 9 and 10 there is shown a method of mounting elastic bands upon the contoured jaw ends of the tweezer. These elastic bands are stored on the wire device shown in FIG. 7. In FIG. 8, one of the elastic bands 75 has been separated from the grouping of bands, shown in FIG. 7, and moved along toward the free or distal end of the wire 76. As seen in FIG. 8, this distal end of the wire has been placed in the groove 70 of the closed ends of the jaws of FIG. 5B.

As seen in FIG. 9, the elastic band 75 has been advanced along the wire 76 to and over the closed, ovoid ends 44a and 45a of the jaws and into the adjacent groove portions 46a and 47a to and against the wall portions 62a and 63a. The inside diameter of the elastic band 75 is slightly less than the combined spherical diameter of the ends 44a and 45a and when this elastic band passes this diameter it slips into and is retained in the groove portions 46a and 47a.

As seen in FIG. 10 the legs or the jaw ends 32a and 34a are starting to be expanded either by means of the residual outward bias built into the tweezer or by manipulation of the lever 42. As depicted, the ends 32A and 34A have been moved apart sufficiently to cause a small stretching of the elastic band 75 to insure its maintenance in the receiving groove in the ends of the tweezer as and while the wire 76 is withdrawn from the groove 70.

INSERTION OF THE ELASTIC BANDS ONTO THE TWEEZER OF FIG. 5

Figure 11:
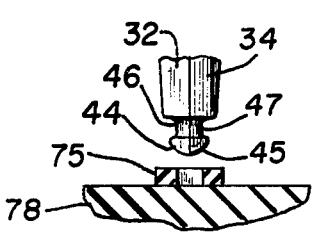
FIG. 11 represents a sectional view, partly diagrammatic and showing a fragmentary view of the contoured jaw ends of the elastic positioner of FIG. 5, this FIG. demonstrating an alternate method of mounting the unstretched elastic bands on the contoured jaw ends.
Figure 12:
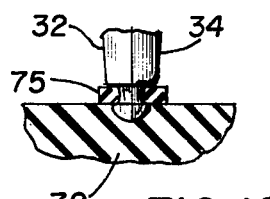
FIG. 12 represents the sectional view of FIG. 11 and showing the alternate method in which a resilient pad or tabletop is used to support the elastic bands as shown, the jaw ends of the elastic positioner have passed through the aperture of the rubber band and the tip of the positioner has slightly entered the band and slightly depressed the resilient tabletop so the rubber band has been slid into the band receiving groove formed adjacent the contoured ends of the jaws.

As seen in FIGS. 11 and 12 it is also to be noted that the elastic bands 75 may be loosely and randomly laid upon a resilient rubber pad 78. As seen in FIG. 11, an elastic band 75 is allowed to lay flat upon the upper surface of this rubber or resilient pad and the end of the tweezer of FIG. 5 is brought adjacent to the aperture formed in the elastic band 75. As seen in FIG. 12, the spherical or ovoid ends 44 and 45 of the tweezer jaws are pressed to and through the inside diameter of the elastic band 75 and into the resilient pad 78. The upper surface of the pad 78 supports the elastic band as the jaw ends are pressed into this resilient pad sufficiently to cause the elastic band to expand sufficiently to slide over the contoured jaw ends and into the adjacent groove. The natural resiliency of the elastic band causes it to be seated in the groove 46 and 47 of the tweezer of FIG. 5. After the elastic band has been seated in this groove the tweezer is lifted from the resilient support pad with the elastic band secured as by a residual bias in the groove on the ends of the tweezer. The nomral spring of the tweezer and the manipulation of the lever 42 enables the tweezer legs to be forced outward to expand the elastic band to its desired expanded condition.

EXPANSION OF THE ELASTIC BAND BY THE CAM BLOCK MEMBER OF FIG. 6

As seen in FIG. 6 and particularly for use with the tweezer-type apparatus of FIGS. 1 and 4, it is contemplated that once the elastic band 75 has been mounted in the groove the bar 42 will then be manipulated to cause the tweezer jaw to be opened and the elastic band to be stretched to its desired open condition. The operator or orthodontist normally utilizes his thumb to engage and move the bar 42 to cause a forward motion and to cause cam block 40 to lift leg 34. This block is moved counterclockwise around the pin 48 and to the position as seen in FIG. 6. In this particular position a flat support surface 50 on the bottom of the cam block 40 engages the comparable flat surface on the jaw member 32 to provide a seated engagement of the block member 40. A short flat portion 88 on the upper surface of cam block member 40 engages the underside of the tweezer leg 34 to also assist the block to be retained in the position of FIG. 6. A camming action is provided by the curved cam surface 52 as the block 40 is rotated counterclockwise. The residual bias in this stretched elastic band 75 urges the two leg members 32 and 34 toward each other and causes this cam block 40 to be maintained in the position of FIG. 6 during the band placement and installation by the orthodontist. Thus secured in the grooved ends of the tweezer legs the expanded elastic band 75 is then ready for use by the orthodontist for securing and installation of the expanded band.

INSTALLATION AS SEEN IN FIG. 13

Figure 13:
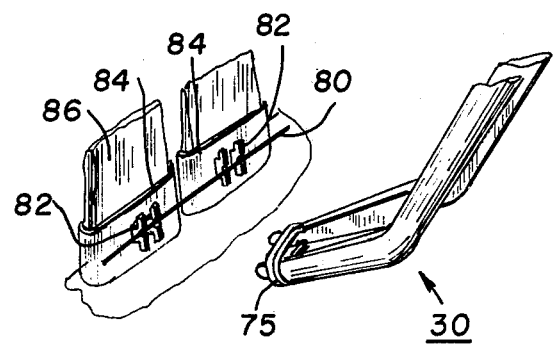
FIG. 13 represents an isometric, partly fragmentary view showing diagrammatically the use of the elastic positioner of FIG. 1 with a stretched rubber band mounted thereon and ready to be moved forward to retain an arch wire upon and within the wire receiving brackets fastened to and carried by two bands mounted upon the teeth of the patient.

As seen in FIG. 13, a wire 80 is placed in retaining clips 82 which are secured to the front foreportions of bands 84 which are shown mounted on teeth 86. With the arch wire placed in the receiving groove of these clips 82, the expanded band 75 is pushed to the position behind the lug portion of the clip 82. Once secured in position behind this lug portion the thumb latch bar 42 is moved rearwardly to allow the band-retaining ends of the positioner to be drawn inwardly by the tension of the expanded band 75, which as it returns toward its original size it is caused to be mounted behind the engaging lug portion of the clip 82 to secure the arch wire 80 in position.

ELASTIC POSITIONER OF FIGS. 14 THROUGH 16

Referring next to FIGS. 14 and 15, there is shown an elastic positioner made by using a forcep or plier-type design. The positioner, as seen in FIGS. 14 and 15 and the ends thereof as shown in FIG. 16, has a pair of plier handles 90 and 91 which are pivotally connected by pin 94. Carried on their distal inner tips 92 and 93 in a split arrangement are the jaw ends which are configured and have an undercut similar to the tip ends such as seen in FIG. 5. In this particular embodiment it is contemplated that a spring 95 carried by pin 96 will urge the jaw tips 92 and 93 into a closed condition for the easy mounting thereon of the elastic bands 75. It is contemplated that, as shown in FIG. 16, the tip ends 92 and 93 are bent at an angle of about thirty degrees from the plane of the handles. Such contoured ends may be used with the resilient rubber pad 78 of FIGS. 11 and 12 or, if desired, a slot may be formed in these contoured tip ends and according to the showing of FIG. 5a a wire form means for retaining and storing elastic bands as in FIG. 7 may be employed. It is contemplated that a limit to the expansion of the plier-type apparatus of FIG. 14 is provided by the pin 96 so that a maximum limit to the expansion of the mounted elastic band is provided.

LATCHING MEANS OF FIG. 17

Referring next to FIG. 17, it is to be noted that the plier-type device of FIGS. 14 and 15 may be provided with a latch, if desired. This latch holds the tips of the plier-type device in an expanded position with the stretched elastic bands mounted thereon. As seen in FIG. 17, arm 91 has a pivoted pin 98 which carries one end of a latching member 100. Latching member 100, in the embodiment of FIG. 17, passes through a cutout 101 in the handle portion of member 92. An abutting edge 102 on member 100 engages the outer surfaces of the handle member 92 and latch 100 is moved counterclockwise around the pivot pin 98. Leaf spring 104 urges latch 100 counterclockwise. As the handle members 91 and 92 are urged toward each other by gripping the handle portion, members 91 and 92 are urged toward each other to cause the tip ends 92 and 93 to be moved outwardly to stretch the bands 75 whereupon as the member 102 passes sufficiently through the cutout 101 in member 90, the spring 104 urges the member 100 counterclockwise around the pin 98 to cause the stop edge 102 to snap into place and prevent the tip ends 92 and 93 to be moved toward each other. To release the tip ends and the mounted, stretched, elastic band thereon, the thumb release 100 is moved clockwise around pin 98 which enables the latching member to slide into cutout 101 and release the arms 90 and 91.

EMBODIMENT OF FIGS. 18 AND 19

In the embodiments of FIGS. 18 and 19 there is shown an alternate latching method wherein a latch member 106 is pivotally carried by pin 107 mounted in a handle member 108. Member 106 is slidable upon the outside of this arm member and likewise slides in a recess formed in handle member 109. Handle members 108 and 109 are pivotally connected by pin 110 and when the handles are brought to band stretching position the arm member 106 swings downwardly counterclockwise as urged by spring 104 to cause shoulder stops 112 to engage the enlarged portion of the handle 109 to provide a latching of the member 106. The recess in handles 108 and 109 enables the latch 108 to be moved clockwise around the pin 107 and shoulder stop 112 to be moved away from the enlarged portion of the handle 109. The handle portions when the stop is released are now also released by the tension in the stretched band and the tip ends are moved into and toward the closed condition whereupon the elastic band may be easily removed from the contoured tip ends.

EMBODIMENT OF FIGS. 20, 21 AND 22

In FIGS. 20, 21 and 22 there is shown yet another alternate construction of a plier-type elastic band positioner such as that shown in FIGS. 14 and 15. This alternate positioner is provided with a spring similar to the spring 95 of FIGS. 14 and 15. In the present embodiment the plier handle members 120 and 121 are pivotally retained by pivot pin 124. By means of spring 125 these jaw members are urged apart. A screw stop 128 is threadedly carried by the arm member 121 which is adjustably set so that the head of the screw provides a stop establishing the maximum opening of the jaw ends 130 of the members 120 and 121. As seen in FIG. 22, the jaw ends 130 are shown as bent at about thirty to forty degrees from the normal plane of the handle members. The ends of these jaw members are configured with an undercut as in the manner of either FIG. 5 or 5A.

EMBODIMENT OF FIGS. 23 AND 24

It is to be noted that in FIG. 23 the jaw members 132 are shown as reduced in size as far as the jaw strength. These are for use with lighter elastic bands whereas in FIG. 24 the jaws themselves are shown made much heavier to provide more strength in the jaw portions 134 and prevent the deflection caused by heavier elastic bands.

EMBODIMENT OF THE ELASTIC BANDS OF FIG. 25

In FIG. 25 is depicted in more-or-less full size scale two of the elastic bands normally used in the practice of orthodontics. These are often referred to as sep-a-rings (trademark of T.P. Laboratories). These sep-a-rings, as mentioned above, are disclosed in U.S. Pat. No. 3,758,947 and pertain to a method for placing stretched bands 175 between adjacent teeth 180 and 181 as in FIG. 26. After a period of time the residual bias of the stretched elastic band causes the teeth to be moved away from each other as in FIG. 27.

Terms such as "left", "right", "up", "down", "bottom", "top", "front", "back", "in", "out", "clockwise", "counterclockwise" and the like are applicable to the embodiments shown and described in conjuction with the drawings. These terms are merely for the purpose of description and do not necessarily apply to the position in which an elastic positioner may be constructed or used.

While particular embodiments of these positioners have been shown and described it is to be understood that modifications may be made within the scope of the accompanying claims and protection is sought to the broadest extent the prior art allows.

What is claimed is:

1. An elastic band positioner having a tweezer configuration with two leg members attached at one end and with the other ends of the legs in a free condition, the positioner particularly for use by orthodontists for receiving, mounting and retaining small elastic bands during expansion, positioning and placing of these bands on arch wire retaining brackets, between teeth and for like uses, said band positioner including: (a) a reduced end portion formed on each of the free ends of the legs and of a reduced size, this pair of legs and these ends movable toward and away from each other in a common plane; (b) a contoured configuration formed on each of the ends of the legs and formed so as to be mirror images of each other and when in a closed side-by-side relationship each leg end provides essentially one-half of an ovoid-shaped configuration whose maximum diameter is easily forced through the passageway of a small elastic band to be mounted and positioned on the closed ovoid-shaped ends of the legs, this ovoid configuration when the legs are in closed condition extending away from the attached ends of the legs and with the curved surface providing a cam and guide for the entrance of the contoured ends to and through the aperture in the elastic bands; (c) a reduced diameter groove formed in the leg ends, this groove immediately adjacent the ovoid configured ends and transverse of a plane bisecting the space between the legs, said groove sized to receive and retain said small elastic band when mounted therein; (d) a shoulder formed on each leg end adjacent this groove, this shoulder providing a stop for inhibiting the unwanted upward travel of the band when placed in said groove, and (e) means for manually moving the legs to an apart condition whereat the mounted band is brought to an expanded condition after which the legs are brought to a closed condition for removal of the band to and on the tooth of the patient, said means including a cam block pivotally carried by one leg of the tweezer and swingable in an arc whose axis is normal to the axis of the leg and in which the other end of the cam block has a cam portion adapted to engage the underside of the opposite leg, this cam block being manipulated from a closed to an open position by means of a manually engaged bar member, one end of said cam block being carried by a spring bar member secured at one end to the leg of the tweezer and with the other end of the spring bar member pivotally retaining and carrying the cam block.

2. An elastic band positioner as in claim 1 in which the cam block has that end which is pivotally mounted to the spring member formed with a flat surface which provides a seating and retaining means for the cam block when it is positioned to maintain the ends of the jaws in an apart condition.

* * * * *